United States Patent
Muse et al.

(10) Patent No.: US 8,408,013 B2
(45) Date of Patent: Apr. 2, 2013

(54) LIGHTWEIGHT PORTABLE MOISTURE TRAPS FOR USE WITH VACUUM PUMPS

(75) Inventors: Peter D. Muse, Durham, NC (US); Johnny Gordon Williams, Jr., Raleigh, NC (US); Ali Regimand, Raleigh, NC (US); Lawrence H. James, Raleigh, NC (US)

(73) Assignee: Instrotek, Inc., Raleigh, NC (US)

( * ) Notice: Subject to any disclaimer, the term of this patent is extended or adjusted under 35 U.S.C. 154(b) by 246 days.

(21) Appl. No.: 12/827,637

(22) Filed: Jun. 30, 2010

(65) Prior Publication Data

US 2012/0000283 A1 Jan. 5, 2012

(51) Int. Cl.
*F25B 21/02* (2006.01)
*F25B 19/00* (2006.01)
*B01D 8/00* (2006.01)
*F26B 13/30* (2006.01)

(52) U.S. Cl. .................. 62/3.4; 62/3.2; 62/3.6; 62/55.5; 62/100; 34/92

(58) Field of Classification Search ............ 62/3.2, 62/3.4, 3.6, 55.5, 100, 169, 268, 270; 96/221
See application file for complete search history.

(56) References Cited

U.S. PATENT DOCUMENTS

| | | | |
|---|---|---|---|
| 560,561 A | 5/1896 | Zappert | |
| 763,388 A | 6/1904 | Gathmann | |
| 2,934,257 A | 4/1960 | Power | |
| 3,423,947 A | 1/1969 | Yosimaro Moriya | |
| 3,643,340 A | 2/1972 | Jackson et al. | |
| 4,107,049 A | 8/1978 | Sano et al. | |
| 4,319,408 A | 3/1982 | Kuboyama | |
| 4,679,402 A * | 7/1987 | Andeen | 62/55.5 |
| 4,686,852 A | 8/1987 | Ito et al. | |
| 4,882,851 A | 11/1989 | Wennerstrum et al. | |
| 5,365,793 A | 11/1994 | Terrel et al. | |
| 5,377,425 A | 1/1995 | Kawakami et al. | |
| 5,546,678 A | 8/1996 | Dhaemers | |

(Continued)

OTHER PUBLICATIONS

Standard Method of Test for "Theoretical Maximum Specific Gravity and Density of Bituminous Paving Mixtures"; Aashto Designation: T 209-94 Methods of Sampling and Testing; pp. 660-667 (1994).

(Continued)

*Primary Examiner* — Frantz Jules
*Assistant Examiner* — Keith Raymond
(74) *Attorney, Agent, or Firm* — Myers Bigel Sibley & Sajovec

(57) ABSTRACT

A portable moisture trap for use with a vacuum pump includes: a housing; a cooling chamber positioned at least partially within the housing including a first inlet port and a second outlet port; a lid that sealably attaches to a top portion of the cooling chamber to seal the cooling chamber; a heat sink residing under the cooling chamber; a thermoelectric device having an upper cooling side and a lower heat generating side residing between the cooling chamber and the heat sink; a fan oriented to blow air upwardly toward the heat sink; and a baffle extending downwardly in the cooling chamber from a location proximate the lid to a location proximate an inner bottom surface of the cooling chamber, with the baffle configured to define a physical barrier to urge air received through the first port to flow down toward the inner bottom surface of the cooling chamber before exiting through the second port, to thereby remove moisture from air traveling through the cooling chamber in response to a vacuum pump in fluid communication with the second port.

18 Claims, 9 Drawing Sheets

U.S. PATENT DOCUMENTS

| | | | |
|---|---|---|---|
| 5,732,478 A | 3/1998 | Chapman et al. | |
| 5,755,039 A | 5/1998 | Mae et al. | |
| 5,819,683 A * | 10/1998 | Ikeda et al. | 118/724 |
| 6,085,443 A | 7/2000 | Hunter et al. | |
| 6,234,008 B1 | 5/2001 | Sjoblom et al. | |
| 6,321,589 B1 | 11/2001 | Regimand | |
| 6,410,889 B2 | 6/2002 | Davis et al. | |
| 6,554,879 B1 | 4/2003 | Nomura | |
| 6,684,684 B2 | 2/2004 | Regimand et al. | |
| 6,817,230 B2 | 11/2004 | James et al. | |
| 7,000,490 B1 * | 2/2006 | Micheels | 73/863.12 |
| 7,021,903 B2 | 4/2006 | Bailey et al. | |
| 7,770,402 B2 * | 8/2010 | Quarre | 62/3.2 |
| 2004/0017563 A1 | 1/2004 | James et al. | |
| 2005/0102851 A1 * | 5/2005 | He et al. | 34/92 |
| 2008/0046047 A1 * | 2/2008 | Jacobs | 607/108 |
| 2010/0319211 A1 | 12/2010 | He et al. | |

OTHER PUBLICATIONS

Standard Test Method for "Theoretical Maximum Specific Gravity and Density of Bituminous Paving Mixtures"; Designation: D2041-00 (ASTM International) pp. 189-192 (2000).

* cited by examiner

LIGHTWEIGHT PORTABLE MOISTURE TRAPS FOR USE WITH VACUUM PUMPS

FIELD OF THE INVENTION

This invention relates to moisture traps, and more particularly to lightweight portable moisture traps for use with vacuum pumps.

BACKGROUND

It is sometimes necessary to evacuate moist air from equipment such as chambers or vessels. For example, a vacuum pump can be used to evacuate air from a chamber containing a moist or wet object. However, if moist air is pulled into a vacuum pump, it can negatively impact the efficiency of the pump and reduce the lifetime of the pump.

In the construction industry, vacuum pumps can be used in the testing of paving materials. By way of example, compacted asphalt samples are tested using ASTM Test D2726, ASTM Test D6752, and AASHTO Test T166. These tests require the determination of the density of the materials. This requires that the dry mass of a sample along with a sample volume be determined in order to calculate the density, which is the ratio of the mass to the volume. Moisture may be introduced into the sample by the cutting process or may be naturally present in the sample. As described in U.S. Patent Application Publication No. 2005/0102851, the disclosure of which is incorporated by reference herein in its entirety, a vacuum pump can be used to remove moisture from a chamber holding the sample to thereby dry the sample.

By way of further example, vacuum pumps can be used in tests to determine the maximum specific gravity and density of bituminous paving mixtures, such as the tests described in ASTM Test D2041 and AASHTO Test T209. In these tests, a sample of known dry weight is placed in a vessel. Water is then introduced into the vessel to submerge the sample, and the vacuum pump evacuates air to reduce the pressure in the vessel. The volume of the sample is then determined, and the density or specific gravity of the sample can be determined based on the dry weight and the volume of the sample.

As seen from these examples, the vacuum pump may evacuate moist air from the chamber or vessel. The evacuated moist air will enter the vacuum pump unless it is dried prior to reaching the pump. Vacuum pumps use lubricants (e.g., oil) to reduce friction between moving parts and to protect seals. However, when moisture enters the vacuum pump, the moisture mixes with the oil and reduces its effectiveness. Thus, moisture will eventually destroy the vacuum pump. Frequent oil changes may prolong the life of the pump, but the oil changes can frustrate the user by increasing cost and creating downtime, and can also produce considerable waste.

Therefore, users sometimes attempt to dry the air before it enters the pump. Indeed, the aforementioned ASTM Test D2041 and AASHTO Test T209 require the use of one or more in-line dryers to reduce moisture entering the vacuum pump. Current practice is to use one or more desiccant air dryers positioned between the equipment containing moist air and the vacuum pump.

However, there are numerous drawbacks to the use of presently used in-line dryers, such as desiccant dryers. First, desiccant dryers can introduce considerable air flow resistance, thereby increasing the power consumed by the vacuum pump and decreasing its efficiency.

Moreover, desiccant dryers can be inefficient with regard to their moisture-removing characteristics. The dryers tend to be most efficient when the desiccants are dry. Thus, the dryers will either lose their efficiency during use or will create downtime while waiting for the desiccants to dry. The dryers could be replaced or recycled during use, but this increases cost and also creates downtime.

Desiccant dryers have a limited lifetime, and need to be replaced or recycled periodically. Again, this increases cost and creates downtime. The continual replacement also produces waste. Furthermore, a user may neglect to timely replace the dryers, which can decrease the efficiency and reduce the life of the vacuum pump.

Thus, the current use of desiccant dryers can be environmentally unfriendly. The dryers increase air flow resistance and can allow moisture into the vacuum pump, which can increase the necessary power consumed by the pump. Moisture entering the pump also reduces the efficiency of the lubricant or oil in the pump, necessitating an increased number of waste-creating oil changes. Finally, because the desiccant dryers inevitably allow moisture to enter the vacuum pump, the life of the vacuum pump is decreased, sometimes substantially. The result can be the early disposal and replacement of pumps.

Therefore, there may be a need for an apparatus that will effectively dry air evacuated from equipment before the air enters the vacuum pump, and will do so without overly restricting air flow. There may be a need for an apparatus that will perform effective drying continuously to minimize downtime. Finally, there may be a need for an environmentally friendly solution that can increase the lifetime of vacuum pumps and generally reduce waste.

SUMMARY

As a first aspect, a portable moisture trap for use with a vacuum pump includes: a housing; a cooling chamber positioned at least partially within the housing including a first inlet port and a second outlet port; a lid that sealably attaches to a top portion of the cooling chamber to seal the cooling chamber; a heat sink residing under the cooling chamber; a thermoelectric device having an upper cooling side and a lower heat generating side residing between the cooling chamber and the heat sink; a fan residing under the heat sink, the fan being oriented to blow air upwardly toward the heat sink; and a baffle extending downwardly in the cooling chamber from a location proximate the lid to a location proximate an inner bottom surface of the cooling chamber. The thermoelectric device is in thermal communication with the cooling chamber and oriented so that the cooling side faces the cooling chamber and the heat generating side faces and is in thermal communication with the heat sink. The baffle is configured to define a physical barrier to urge air received through the first port to flow down toward the inner bottom surface of the cooling chamber before exiting through the second port, to thereby remove moisture from air traveling through the cooling chamber in response to a vacuum pump in fluid communication with the second port.

In some embodiments, the baffle includes a plate that extends across the cooling chamber so that the first port is on one side of the plate and the second port is on the other side of the plate. The plate has a bottom edge with alternating downward projections and valleys that resides proximate the inner bottom surface of the cooling chamber.

As a second aspect, a method of determining the maximum specific gravity or density of a sample of paving mixture includes: providing a portable moisture trap in a fluid path connecting a vessel adapted to hold a test sample and a vacuum pump, wherein the portable moisture trap includes a cooling chamber having a first port connected to the vessel and a second port connected to the vacuum pump, and wherein the portable moisture trap further includes a thermoelectric device; cooling the cooling chamber of the portable moisture trap using the thermoelectric device; weighing the test sample to determine a dry mass of the sample; placing the test sample in the vessel; adding water to the vessel to submerge the test sample; then evacuating moist air from the vessel while the test sample is submerged using the vacuum pump; then determining a volume of the test sample; and calculating the density and/or the maximum specific gravity of the test sample using the determined dry mass and the determined volume of the sample. The evacuating step is carried out by: flowing the moist air from the vessel through the first port of the cooling chamber; then removing moisture from the moist air in the cooling chamber; and then flowing substantially dry air through the second port of the cooling chamber toward the vacuum pump.

In some embodiments, determining the volume of the sample includes: submerging the vessel with the test sample in a water bath; and determining an underwater weight of the test sample. In some other embodiments, determining the volume of the sample includes: filling a known volume vessel with the sample and water; and weighing the filled vessel in air.

In some embodiments, the cooling chamber includes a baffle extending downwardly in the cooling chamber from a location proximate a lid to a location proximate an inner bottom surface of the cooling chamber. The step of removing moisture from the moist air in the cooling chamber includes urging moist air down toward the inner bottom surface of the cooling chamber. In some embodiments, the baffle includes a plate that extends across the cooling chamber so that the first port is on one side of the plate and the second port is on the other side of the plate, wherein the plate has a bottom edge with alternating downward projections and valleys that resides proximate the inner bottom surface of the cooling chamber. The step of removing moisture from the moist air in the cooling chamber includes flowing moist air through the valleys of the baffle.

As a third aspect, a system for evaluating test samples includes: a chamber containing moist air and adapted to hold a loose aggregate or compacted asphalt sample; a vacuum pump in fluid communication with the chamber to evacuate moist air from the chamber; a fluid path connecting the chamber and the vacuum pump; and a portable moisture trap positioned in the fluid path to remove moisture from the evacuated air. The portable moisture trap includes: a housing; a cooling chamber at least partially within the housing including a first port and a second port; a lid that sealably attaches to a top portion of the cooling chamber to seal the cooling chamber; a heat sink residing under the cooling chamber; a thermoelectric device having an upper cooling side and a lower heat generating side residing between the cooling chamber and the heat sink; a fan residing under the heat sink and oriented to blow air upwardly to remove heat from the heat sink; and a baffle extending downwardly in the cooling chamber from a location proximate the lid to a location proximate an inner bottom surface of the cooling chamber. The thermoelectric device is in thermal communication with the cooling chamber and oriented so that the cooling side faces the cooling chamber and the heat generating side faces and is in thermal communication with the heat sink. The baffle is configured to define a physical barrier to urge air received through the first port to flow down toward the inner bottom surface of the cooling chamber before exiting through the second port. In operation and in response to operation of the vacuum pump, moist air flows from the chamber through the first port of the cooling chamber, down and adjacent the inner bottom surface of the cooling chamber to remove moisture from the moist air, and substantially dry air flows through the second port of the cooling chamber to the vacuum pump.

In some embodiments, the baffle includes a plate that extends across the cooling chamber so that the first port is on one side of the plate and the second port is on the other side of the plate. The plate has a bottom edge with alternating downward projections and valleys that resides proximate the inner bottom surface of the cooling chamber. In operation, moist air flows through the valleys and adjacent the inner bottom surface of the cooling chamber to remove moisture from the moist air.

As a fourth aspect, a system for drying a compacted asphalt sample includes: a sealable chamber including an interior to house the compacted asphalt sample; a first valve in communication with a first port of the chamber; a second valve in communication with a second port of the chamber; a vacuum pump in communication with the chamber to evacuate air from the interior of the chamber through the second port of the chamber; a fluid path connecting the chamber and the vacuum pump; a portable moisture trap positioned in the fluid path to remove moisture from the evacuated air including a cooling chamber having a first port in fluid communication with the chamber and a second port in fluid communication with the vacuum pump and also including a thermoelectric device to cool the cooling chamber; and a controller. The controller is configured to: open and close the first and second valves; operate the vacuum pump; operate the thermoelectric device of the portable moisture trap; cycle the system between a first mode and a second mode, wherein during the first mode the first valve is closed, the second valve is open, and the vacuum pump is operated such that the vacuum pump evacuates air from the interior of the chamber, through the second port of the chamber, through the portable moisture trap, and to the vacuum pump, and wherein during the second mode the first valve is open and air is supplied through the first port of the chamber to the interior of the chamber; and monitor vacuum pressure in the interior of the chamber until the pressure drops below 10 TORR. In operation during the first mode, moist air flows through the second port of the chamber, through the first port of the cooling chamber of the moisture trap and adjacent an inner bottom surface of the cooling chamber to remove moisture from the moist air such that substantially dry air flows through the second port of the cooling chamber of the moisture trap and to the vacuum pump.

In some embodiments, the portable moisture trap includes a solid metal baffle with a bottom edge having alternating projections and valleys adjacent the inner bottom surface of the cooling chamber. In operation during the first mode, moist air flows through the valleys and adjacent the inner bottom surface of the cooling chamber to remove moisture from the moist air.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner.

These and other objects and/or aspects of the present invention are explained in detail in the specification set forth below.

DETAILED DESCRIPTION OF EMBODIMENTS OF THE INVENTION

Figure 1:
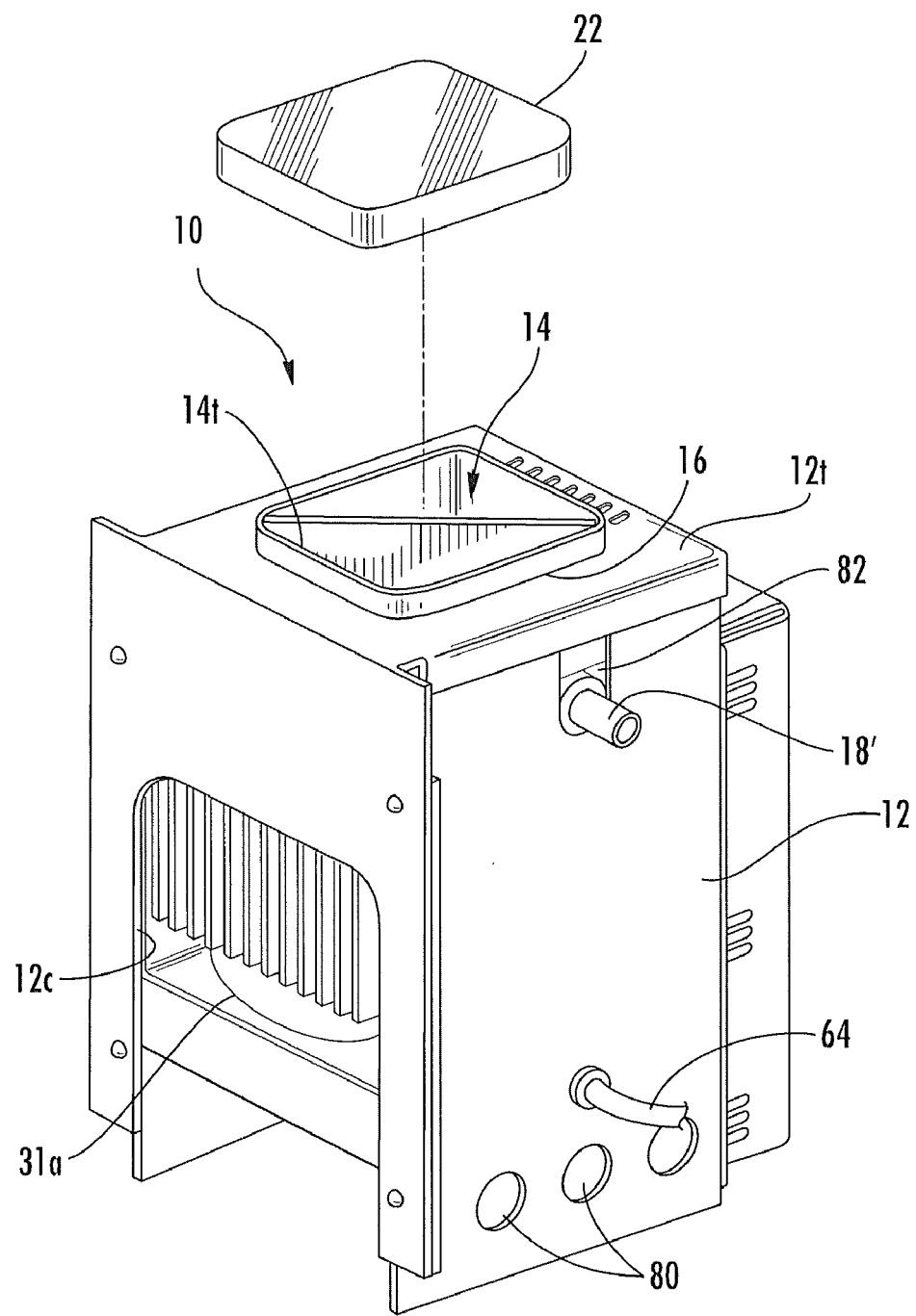
FIG. 1 is a front perspective view of a moisture trap including a housing according to some embodiments of the invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit of flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

As used herein, the term "housing" means one or more panels generally defining an outer structure relative to one or more components of a moisture trap. The housing can include panels such as sidewalls and/or a top portion, but these panels need not fully enclose any components. As used herein, the term "in the housing" means that sidewall panels generally surround a component but are not necessarily in contact with the component.

FIG. 1 illustrates a moisture trap 10 according to some embodiments of the invention. The moisture trap 10 includes a housing 12. A cooling chamber 14 is positioned at least partially in the housing 12. In some embodiments, the cooling chamber 14 is held by the housing 12. The housing 12 includes a top portion 12t having an aperture 16 through which the cooling chamber 14 can be accessed. An open top portion 14t of the cooling chamber 14 can be located within the housing 12, can be substantially flush with the top portion 12t of the housing 12, or can extend through the aperture 16 and through the top portion 12t of the housing 12.

Figure 2:
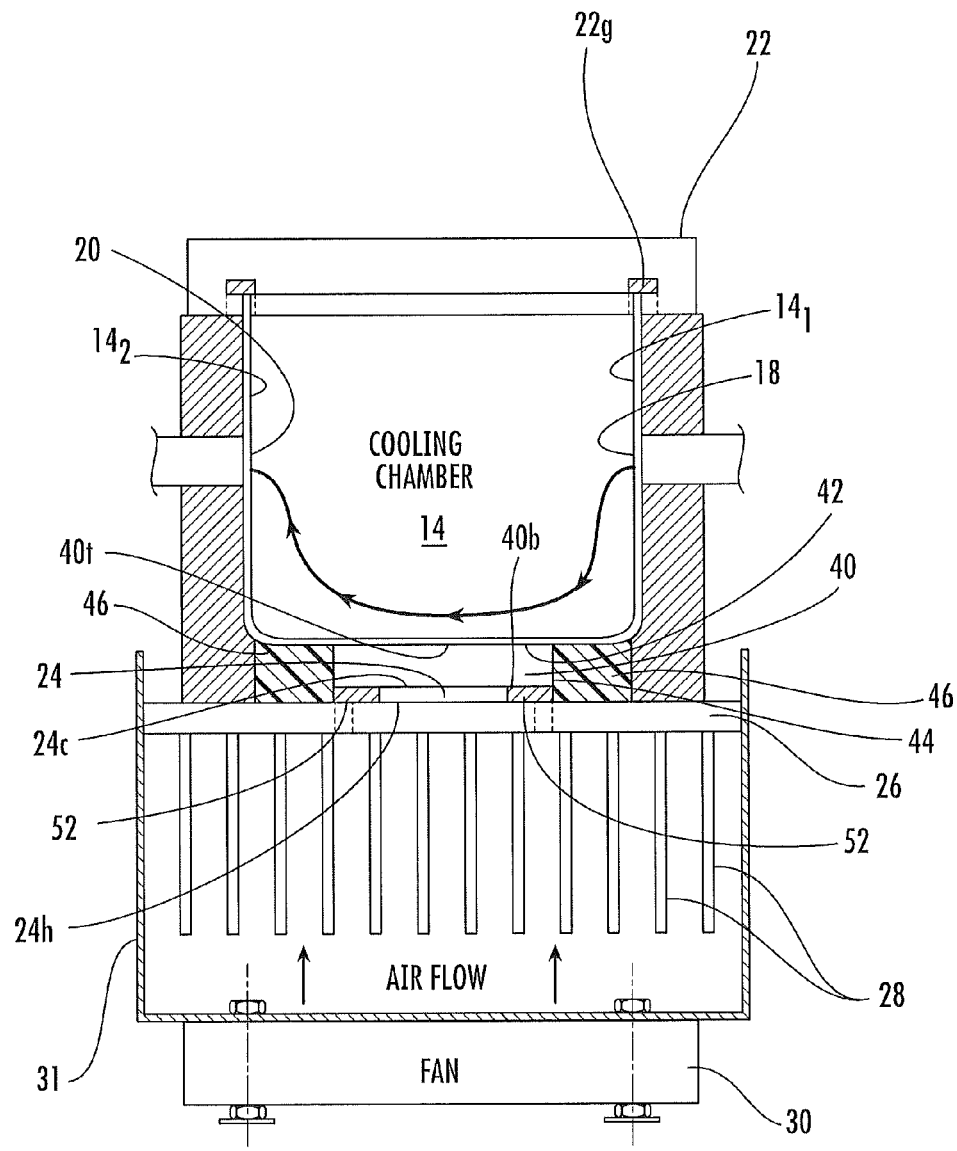
FIG. 2 is a front cross-sectional view of the moisture trap of FIG. 1 with the housing removed.

FIG. 2 illustrates certain components of the moisture trap 10 with the housing 12 removed according to some embodiments of the invention. The cooling chamber 14 includes a first port 18 and a second port 20. As illustrated, the first port 18 extends through a first side or sidewall $14_1$ of the cooling chamber 14 and the second port 20 extends through an opposing second side or sidewall $14_2$ of the cooling chamber 14. As will be described in more detail below, connectors 18', 20' (FIGS. 1, 3A-3C, 5 and 6) may extend from the ports 18, 20 (e.g., the connectors 18', 20' may extend outside the housing 12).

The moisture trap 10 includes a cover or lid 22 to cover the open top portion 14t of the cooling chamber 14. The lid 22 is configured to pivotably or sealably connect to the top portion 14t of the cooling chamber 14. In position, the lid 22 can provide an airtight seal over the top portion 14t of the cooling chamber 14. In some embodiments, the lid 22 includes a gasket 22g to sealably connect to the top portion 14t of the cooling chamber 14. In some embodiments, the lid 22 includes an optically translucent or transparent material and is configured to allow a user to view the interior of the cooling chamber 14.

A thermoelectric device 24 resides under the cooling chamber 14. In some embodiments, the thermoelectric device 24 is positioned in the housing 12. As understood by those of ordinary skill in the art, thermoelectric devices (also known as Peltier devices) can be activated by a voltage supply to create opposing heat generating and cooling sides. Exemplary thermoelectric devices are available from TE Technology, Inc. in Traverse City, Mich. In the illustrated embodiment, the thermoelectric device 24 includes an upper cooling side 24c and a lower heat generating side 24h. The thermoelectric device 24 is in thermal communication with the cooling chamber 14 and oriented so that the cooling side 24c faces the cooling chamber 14.

The moisture trap 10 also includes a heat sink 26 residing under the thermoelectric device 24. In some embodiments, the heat sink 26 is positioned at least partially in the housing 12. The thermoelectric device 24 is positioned between the cooling chamber 14 and the heat sink 26. The heat generating side 24h of the thermoelectric device 24 faces and is in thermal communication with the heat sink 26. More particularly, the heat generating side 24h of the thermoelectric device 24 can be in contact with an upper surface of the heat sink 26. In some embodiments, the heat sink 26 includes elongated downwardly extending fins 28. As understood by those of skill in the art, the fins 28 provide increased surface area and can facilitate heat transfer.

A fan 30 is configured to remove heat from the heat sink 26. In some embodiments, the fan 30 is positioned at least partially in the housing 12. As illustrated, the fan 30 resides below the heat sink 26 and is oriented in a substantially horizontal configuration and is configured to blow air upwardly toward the heat sink 26 and/or the elongated fins 28. The fan 30 may be attached to a bracket 31 (for example, with bolts, rods, or the like), and the bracket 31 may be attached to the housing 12. The bracket 31 may include an aperture 31a (FIG. 1) through which air may flow. It is noted that the bracket is optional and the fan 30 may be situated under the heat sink 26 in other ways (for example, the fan 30 may be directly mounted to the housing 12). It is further noted that the fan need not be in a horizontal configuration. For example, the fan may be oriented vertically, or at any angle between horizontal and vertical, and duct work may direct air flow toward the heat sink 26 and/or the elongated fins 28.

In some embodiments, the housing 12 includes a sidewall having a cutaway 12c (FIG. 1). The cutaway 12c has a size sufficient to expose at least a major portion of a length of the downwardly extending fins 28 to environmental conditions. The cutaway 12c can improve airflow and enhance heat transfer away from the heat sink 26.

The cutaway 12c can also allow for sufficient intake of environmental air to the fan 30. Additionally or alternatively, sidewalls of the housing 12 can include apertures 80 (FIGS. 1 and 6) can allow for sufficient intake of air to the fan 30.

As understood by those of skill in the art, the temperature of the cooling side 24c of the thermoelectric device 24 decreases as more heat is dissipated from the heat generating side 24h of the thermoelectric device 24. Therefore, as the heat generating side 24h is in thermal communication with the heat sink 26, increased heat transfer away from the heat sink 26 will result a colder cooling side 24c of the thermoelectric device 24.

The moisture trap 10 includes a baffle configured define a physical barrier to urge air received from one of the ports 18, 20 to flow down toward the inner bottom surface 34 of the cooling chamber 14 before exiting through the other of the ports 18, 20, as will be described in more detail below. The baffle may comprise piping, mesh material, one or more plates, or one or more chambers within the interior of the cooling chamber 14.

Figure 3A:
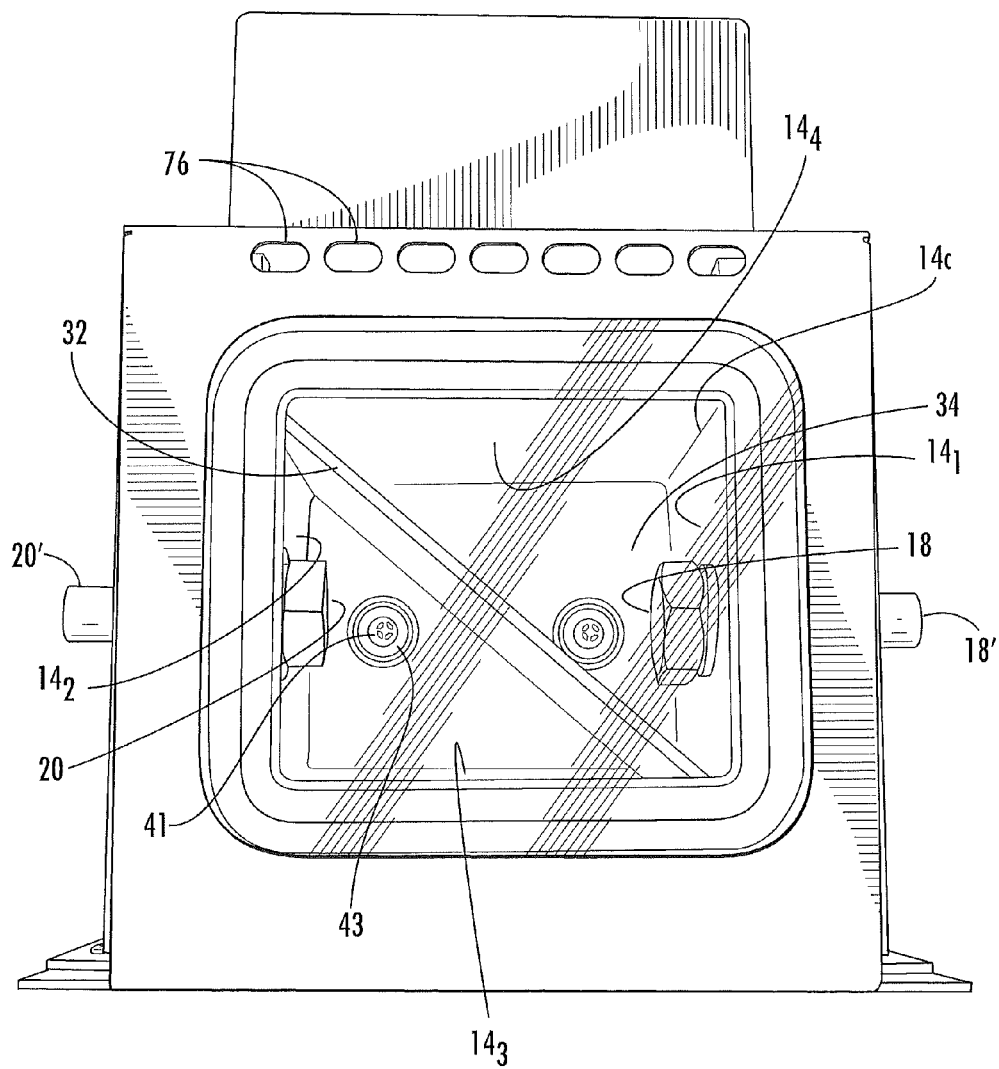
FIG. 3A is a top view of the moisture trap of FIG. 1.

FIG. 3A is a top view of the moisture trap 10 according to some embodiments of the invention. As illustrated, a baffle 32 extends downwardly in the cooling chamber 14 from a location proximate the lid 22 (or the top portion 14t of the chamber 14) to a location proximate an inner bottom surface 34 of the cooling chamber 14. The baffle 32 can be a plate sized and configured to extend across the cooling chamber 14 such that the first port 18 is on one side of the baffle 32 and the second port 20 is on the opposite side of the baffle 32. In some embodiments, the baffle 32 may contact opposing corners or sidewalls of the cooling chamber 14.

The cooling chamber 14 can be substantially square or rectangular. The first and second sides or sidewalls $14_1$, $14_2$ of the cooling chamber 14 can be substantially parallel. The cooling chamber can include third and fourth sides or sidewalls $14_3$, $14_4$ attached to the first and second sides $14_1$, $14_2$, and the third and fourth sidewalls $14_3$, $14_4$ can be substantially parallel. The first port 18 may extend through one sidewall and the second port 20 may extend through an opposing sidewall. For example, as illustrated in FIG. 3A, the first port 18 may extend through the first sidewall $14_1$ of the cooling chamber 14 and the second port 20 may extend through the opposing second sidewall $14_2$ of the cooling chamber.

As illustrated in FIG. 3A, the baffle 32 may extend diagonally across the cooling chamber 14 and contact opposing corners or sidewalls. As illustrated, the baffle 32 extends from or adjacent a corner defined by sidewalls $14_1$, $14_3$ to or adjacent a corner defined by sidewalls $14_2$, $14_4$. In some other embodiments, the baffle 32 may extend diagonally from or adjacent a corner defined by sidewalls $14_1$, $14_4$ to or adjacent a corner defined by sidewalls $14_2$, $14_3$. In any event, the baffle 32 can be sized and configured to fit within the cooling chamber 14 such that the first port 18 is on one side of the baffle 32 and the second port 20 is on the opposite side of the baffle 32.

Figure 3B:
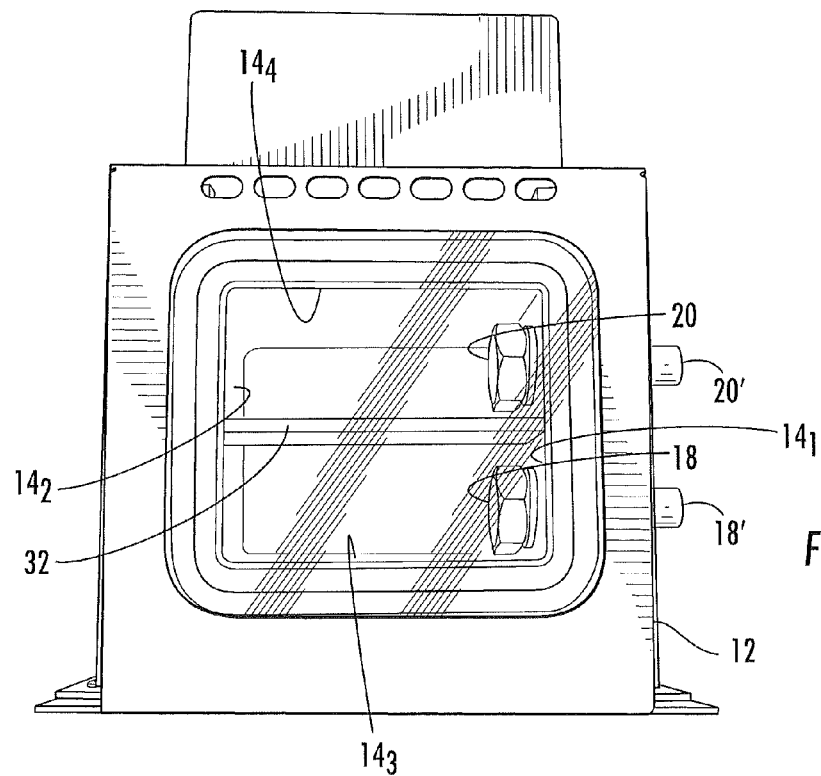
FIGS. 3B and 3C are top views illustrating alternative port locations and alternative baffle configurations for the moisture trap of FIG. 1 according to some embodiments of the invention.
Figure 3C:
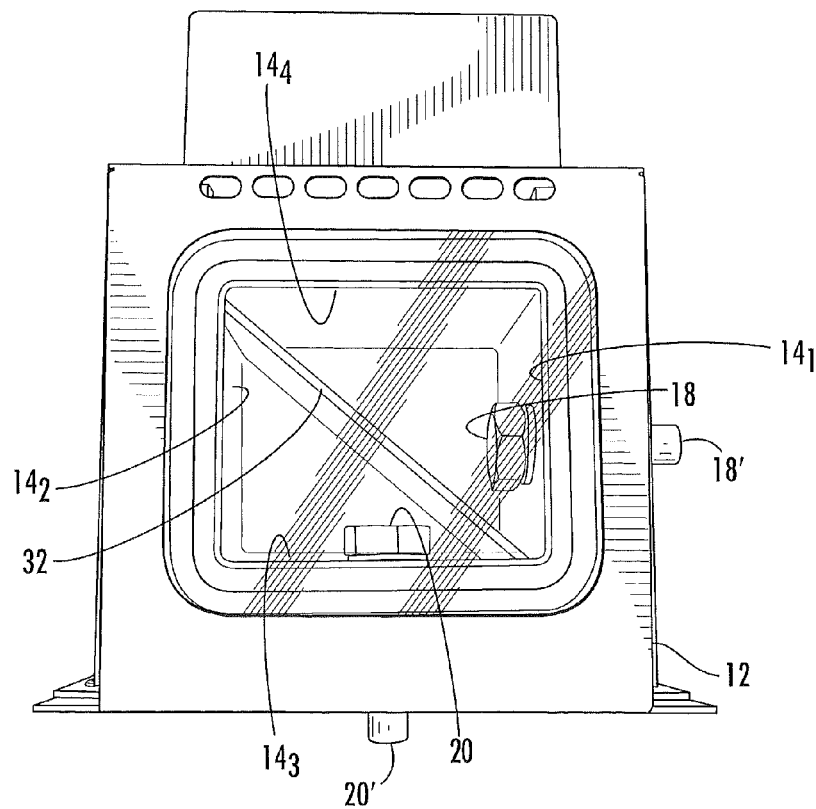

FIGS. 3B and 3C are top views illustrating port and baffle configurations according to some other embodiments of the invention. For example, the first and second ports 18, 20 may extend through the same sidewall of the cooling chamber 14 as illustrated in FIG. 3B. In the illustrated embodiment, the first and second ports 18, 20 extend through the first sidewall $14_1$ and the baffle 32 is sized and configured to extend across the cooling chamber 14 and contact opposing sidewalls $14_1$, $14_2$ such that the first port 18 is on one side of the baffle 32 and the second port 20 is on the opposite side of the baffle 32. The ports 18, 20 can also both extend through any of sidewalls $14_2$, $14_3$, $14_4$, and the baffle 32 can be sized and configured to contact opposing sidewalls such that the first port 18 is on one side of the baffle 32 and the second port 20 is on the opposite side of the baffle 32.

In some other embodiments, the first port 18 may extend through one sidewall of the cooling chamber 14 and the second port 20 may extend through an adjacent sidewall of the cooling chamber 14. As illustrated in FIG. 3C, the first port 18 may extend through the first sidewall $14_1$ of the cooling chamber and the second port 20 may extend through the adjacent third sidewall $14_3$ of the cooling chamber 14 (it will be understood that the ports 18, 20 may extend through any adjacent sidewalls). As illustrated and as described above in reference to FIG. 3A, the baffle 32 can extend diagonally across the cooling chamber 14 and can be sized and configured to fit within the cooling chamber 14 such that the first port 18 is on one side of the baffle 32 and the second port 20 is on the opposite side of the baffle 32.

It will be understood that the ports 18, 20 may be at the same or substantially the same vertical level or elevation (e.g., relative to the ground or the inner bottom surface 34 of the cooling chamber 14), or may be at different vertical levels or elevations.

It will further be understood that, although not illustrated, one or both of the ports 18, 20 may extend through the top of the cooling chamber 14 (e.g., through or adjacent the lid 22)

and/or one or both of the ports 18, 20 may extend through the bottom of the cooling chamber 14 (e.g., through the inner and/or outer bottom surfaces 34, 42).

Figure 4:
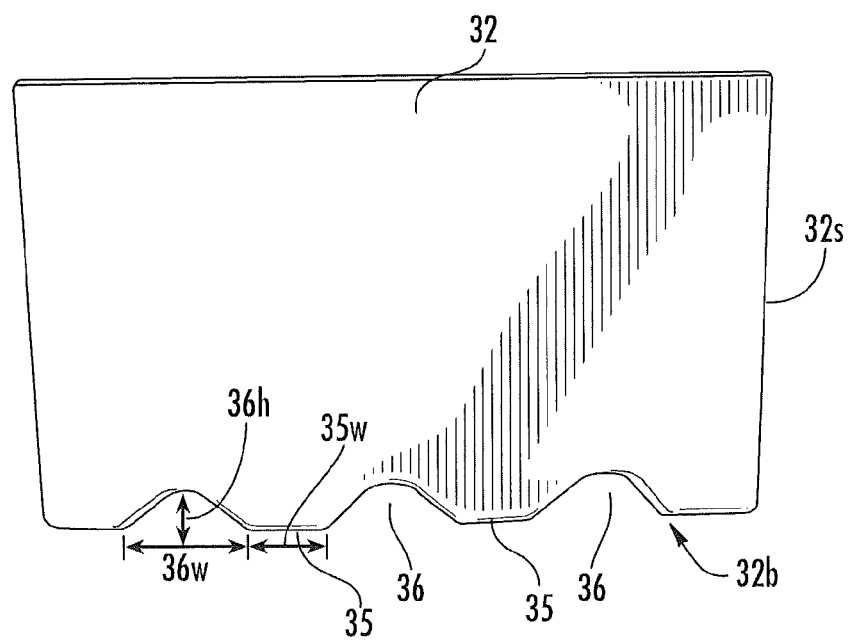
FIG. 4 illustrates a baffle for use with the moisture trap of FIG. 1 according to some embodiments of the invention.

FIG. 4 is a side view of the baffle 32 according to some embodiments of the invention. The baffle 32 has a bottom edge 32b with alternating downward projections 35 and valleys 36 (i.e., openings between the projections). At least some of the projections 35 (and perhaps all of the projections 35, or all of the projections 35 aside from the outermost projections 35) can have a width 35w of about 1 inch. At least some of the valleys 36 (and perhaps all of the valleys 36) can have a width 36w of about 0.47 inches. At least some of the valleys 36 (and perhaps all of the valleys 36) can have a height 36h of about 0.35 inches.

The baffle 32 can be slidably inserted into the interior of the cooling chamber 14, as shown in FIGS. 3A-3C. When inserted, the bottom edge 32b of the baffle 32 resides proximate the inner bottom surface 34 of the cooling chamber 14. Opposing sides 32s of the baffle and/or interior corners 14c of the cooling chamber 14 may be rounded to facilitate insertion of the baffle 32 into the chamber 14. In some other embodiments, the interior of the chamber 14 may include grooves (not shown) to facilitate insertion of the baffle 32. Alternatively, the baffle 32 may be integrated with the interior of the chamber 14. The baffle 32 may be a corrosion-resistant metal plate (e.g., aluminum or stainless steel) and may have a thickness of between about 0.032 inches to about 0.25 inches.

Referring again to FIG. 2, in some embodiments, the moisture trap 10 may include a spacer block 40 positioned between the cooling side 24c of the thermoelectric device 24 and an outer bottom surface 42 of the cooling chamber 14. As will be described in more detail below, the spacer block 40 can be used on top of the thermoelectric device 24 to help isolate the cooling chamber 14 from the heat generating side 24h of the thermoelectric device 24. Furthermore, as will be described in more detail below, insulation can be placed proximate the spacer block 40 to help further isolate the cooling chamber 14 from the heat generating side 24h of the thermoelectric device 24 and/or the heat sink 26.

Therefore, in some embodiments, the heat sink 26, the thermoelectric device 24, the spacer block 40, and the cooling chamber 14 can comprise a stackable assembly as illustrated. The assembly or stack can be tightened together firmly to attain good surface-to-surface contact and enhance thermal transfer. The cooling chamber 14 may be firmly attached to the spacer block 40 in a manner known to those of ordinary skill in the art. By way of example, one or more fasteners 41 (e.g., screws) may penetrate through the chamber 14, spacer block 40, and into apertures (e.g., threaded apertures) in the heat sink 26 (FIG. 3A). Vacuum sealing washers 43 may also be used as illustrated (FIG. 3A). Moreover, thermally conductive paste and/or film may be applied or positioned between the heat sink 26 and the heat generating side 24h of the thermoelectric device 24, between the cooling side 24c of the thermoelectric device 24 and a bottom surface 40b of the spacer block 40, and/or between an top surface 40t of the spacer block 40 and the outer bottom surface 42 of the cooling chamber 14 to further enhance thermal transfer. Exemplary foil is available from Graphite Foil Fabricators Corp. in Plantsville, Conn. Exemplary paste is available from Arctic Silver Corp. in Visalia, Calif.

As illustrated in FIG. 2, the thermoelectric device 24 can have a cross-sectional area that is less than a cross-sectional area of the spacer block 40, and the thermoelectric device 24 can have a thickness that is less than a thickness of the spacer block 40. Also as illustrated, the spacer block 40 can have a cross-sectional area that is less than a cross-sectional area of the cooling chamber 14 (i.e., the area of the outer bottom surface 42 of the cooling chamber 14). In some embodiments, the thermoelectric device 24 is substantially centered above the heat sink 26, the spacer block 40 is substantially centered above the thermoelectric device 24, and/or the cooling chamber 14 is substantially centered above the spacer block 40.

The thermoelectric device 24 can have a surface area (e.g., on the cooling side 24c) that is less than about 2.5 square inches and can be less than about 0.25 inches thick (or, in some embodiments, less than about 0.15 inches thick). The spacer block 40 can have a surface area (e.g., on the bottom surface 40b) that is less than about 4 square inches and can be less than about 0.75 inches thick (or, in some embodiments, less than about 0.5 inches thick). The outer bottom surface 42 of the cooling chamber 14 can have a surface area of less than about 15 square inches. More particularly, the cooling chamber 14 can have cross-sectional dimensions of about 4 inches by about 3.5 inches. The cooling chamber 14 can have a height of between about 1 inch to about 5 inches. Thus, the cooling chamber 14 can have an internal volume of about 14 cubic inches to about 70 cubic inches. These relatively small component dimensions allow for a lightweight and portable design, as described in more detail below.

A first insulating material 46 can snugly surround downwardly extending perimeter sides 44 of the spacer block 40. In some embodiments, the insulating material 46 is a gasket, with an upper portion of the gasket 46 directly contacting the outer bottom surface 42 of the cooling chamber 14 and a lower portion of the gasket 46 directly contacting an upper surface of the heat sink 26. The insulating material 46 can be foam rubber, such as polyurethane foam, foam rubber latex, and the like. In the illustrated embodiment, the spacer block 40 has a larger surface area than the thermoelectric device 24, thereby forming gaps or spaces 52 between the spacer block 40 and the heat sink 26. The insulating material or gasket 46 can be formed to fill the gaps 52. Alternatively, the gaps 52 may remain open or may be filled with additional insulating material.

The first insulating material 46 can further thermally isolate the cooling chamber 14 from the heat generating side 14h of the thermoelectric device 24 and the heat sink 26. In some embodiments, the insulating material 46 contacts the outer bottom surface 42 of the cooling chamber 14 and extends outwardly to the first and second sides or sidewalls $14_1$, $14_2$ and/or to the third and fourth sides or sidewalls $14_3$, $14_4$ of the cooling chamber 14. In this regard, the spacer block 40 and the insulating material 46 can serve to help thermally isolate the outer bottom surface 42 of the cooling chamber 14 from the thermoelectric device 24 and the heat sink 26. In some embodiments, the insulating material 46 is less than about 3 inches thick and, in some embodiments, less than about 2.5 inches thick.

As seen in FIG. 3A, the cooling chamber 14 can be spaced apart from sidewalls of the housing 12. In some embodiments, the heat sink 26 has a larger surface area than the surface area of the outer bottom surface 42 of the cooling chamber 14. For example, the heat sink 26 may extend proximate sidewalls of the housing 12. Therefore, it may be desirable to further insulate the cooling chamber 14 from the exposed portions of the heat sink 26 (e.g., those portions not thermally isolated from the cooling chamber 14 by the first insulating material 46).

Figure 5:
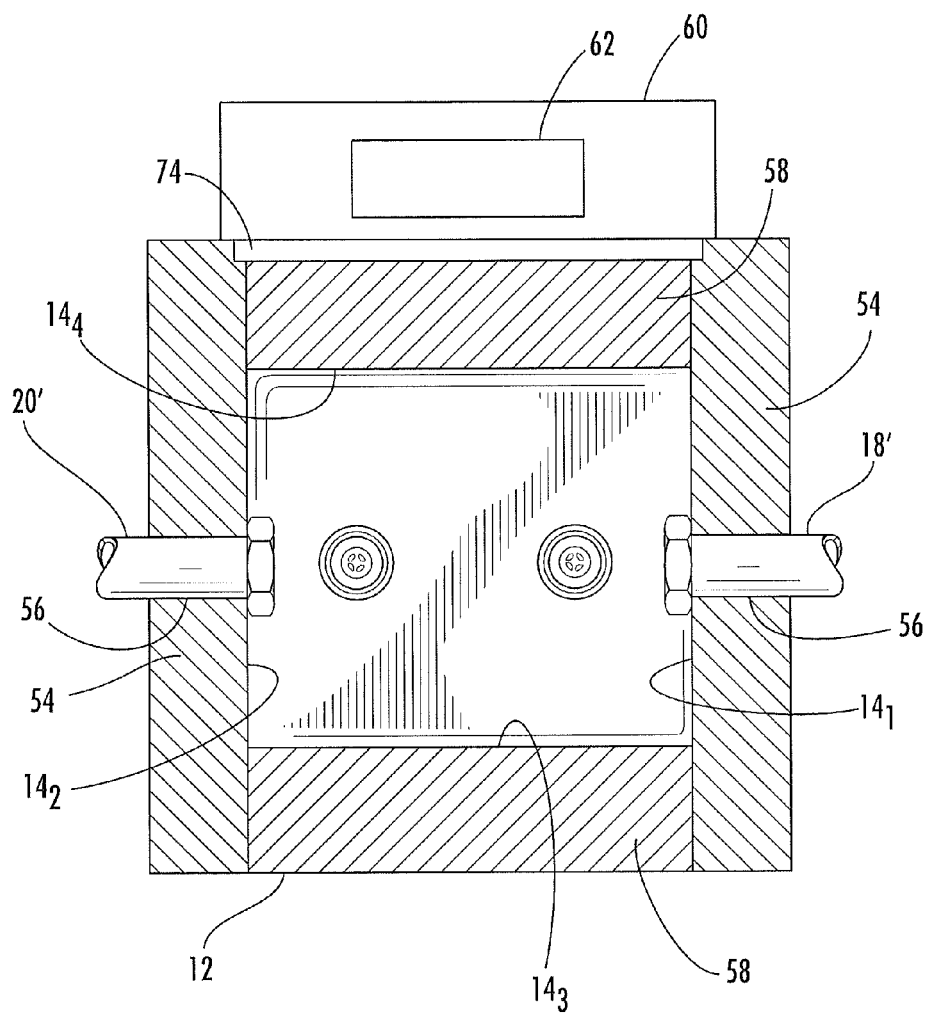
FIG. 5 is a top cross-sectional view of the moisture trap of FIG. 1 according to some embodiments of the invention.

FIG. 5 illustrates the moisture trap 10 with the top portion 12t of the housing 12 removed according to some embodiments. A second insulating material 54 can be positioned between the first and second sidewalls $14_1$, $14_2$ of the cooling chamber 14 and the housing 12. The second insulating material 54 may be the same as the first insulating material 46 or may be different. In some embodiments, the second insulating material 54 comprises fiberglass. The second insulating material 54 can extend downwardly along the entire first and second sidewalls $14_1$, $14_2$ of the cooling chamber 14 and, in some embodiments, can extend downwardly to the upper surface of the heat sink 26. The second insulating material 54 may be about 1 inch thick (and therefore the space between the first and second sidewalls $14_1$, $14_2$ of the cooling chamber 14 and the housing 12 may be about 1 inch). The second insulating material 54 can include apertures 56 through which the first and second connectors 18', 20' extend.

A third insulating material 58 can be positioned between the third and fourth sidewalls $14_3$, $14_4$ of the cooling chamber 14 and the housing 12. The third insulating material 58 may be the same or different from the first insulating material 46 and/or the second insulating material 54. In some embodiments, the third insulating 58 material comprises foam rubber, such as polyurethane foam, foam rubber latex, and the like. The third insulating material 58 can be adhesively attached to the third and fourth sidewalls $14_3$, $14_4$ of the cooling chamber 14. The third insulating material 58 can extend downwardly along the entire third and fourth sidewalls $14_3$, $14_4$ of the cooling chamber 14 and, in some embodiments, can extend downwardly to the upper surface of the heat sink 26. The third insulating material 58 may be about 1 inch thick (and therefore the space between the third and fourth sidewalls $14_3$, $14_4$ of the cooling chamber 14 and the housing 12 may be about 1 inch). The third insulating material 58 can include apertures (not shown) through which the first and second connectors 18', 20' may extend.

Figure 6:
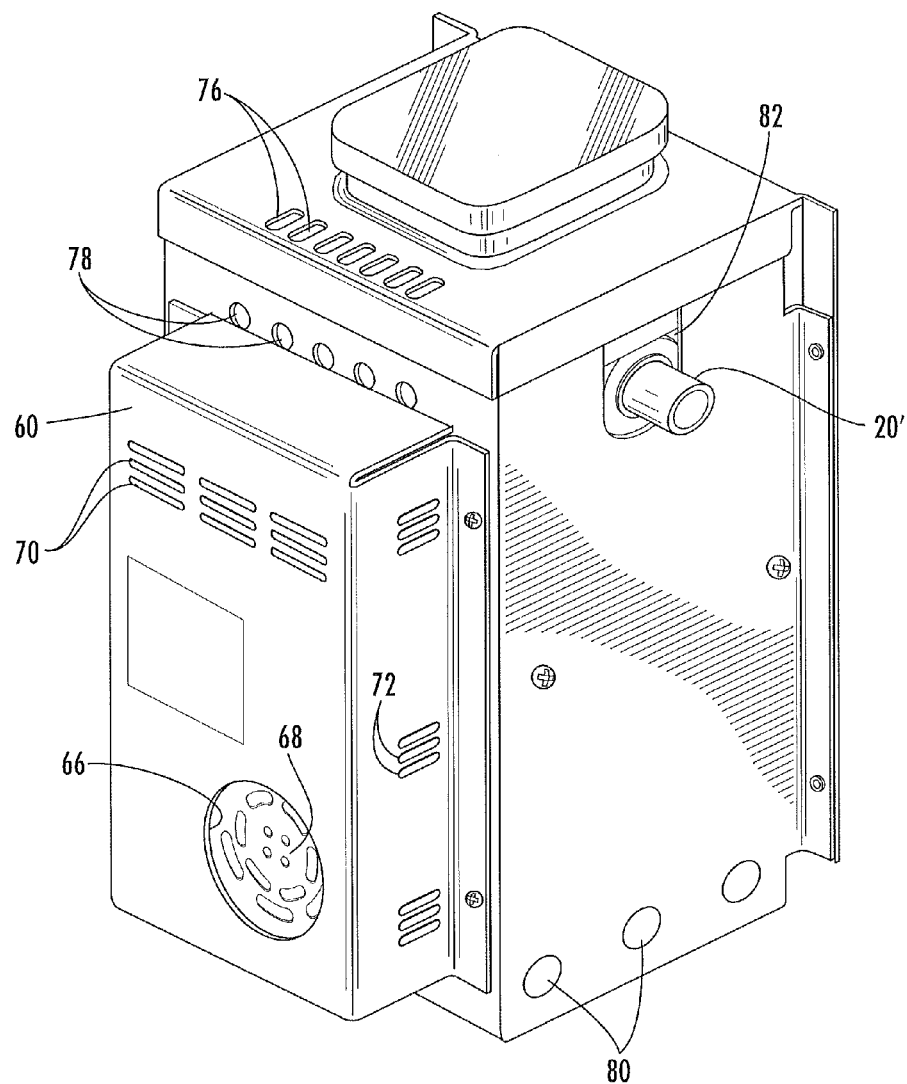
FIG. 6 is a rear perspective view of the moisture trap of FIG. 1.

FIG. 6 is a rear perspective view of the moisture trap 10. A power supply box 60 can be attached to the housing 12 (in some embodiments, the box 60 may be integrated with the housing 12). The box 60 can house a power adapter 62 (FIG. 5) to convert AC power to DC power. For example, the adapter 62 may convert about 120 volts AC to about 15 volts DC. A power cord 64 (FIG. 1) can supply AC power to the moisture trap 10. The power cord 64 can run into the box 60 to supply AC power to the adapter 62; for example, the cord 64 may run adjacent the fan 30 and into the box 60. DC power from the power adapter 62 can be used to supply power to the thermoelectric device 24 and/or to the fan 30. The box 60 can include an aperture 66 to provide air to a fan 68 to cool the power adapter 62 and its associated components. The fan 68 may be integrated with the power adapter 62 or may be a separate component. The box 60 can include apertures 70, 72 for additional cooling and/or air flow. The adapter 62 can be positioned in the box 60 such that it is spaced apart from the housing 12. This space can serve to thermally isolate the adapter 62 from the heat sink 26 and other components of the moisture trap 10. In some embodiments, the adapter 62 may be spaced at least about 0.1875 inches from the housing 12.

Referring to FIG. 5, in some embodiments, there may be a gap 74 between the insulating material 58 and the housing 12 adjacent the power supply box 60. The gap 74 may allow air from the fan 30 to pass through the heat sink 26, up along the housing 12 and through apertures 76, 78 in the housing 12 (FIG. 6). In this regard, the gap 74 and apertures 76, 78 can help dissipate additional heat from the heat sink 26, thereby allowing for a colder cooling side 24c of the thermoelectric device 24 and in turn a colder cooling chamber 14. Moreover, the gap 74 can thermally isolate the box 60 and the power adapter 62 from the heat sink 26 and other components of the moisture trap 10. Where used, the gap 74 will typically have a thickness of less than about 0.50 inches.

As described above, the moisture trap 10 can include connectors 18', 20' (FIGS. 1, 3A-3C, 5 and 6). The connectors 18', 20' may connect with, extend through, and/or be integrated with respective ports 18, 20 of the cooling chamber 14. The connectors 18', 20' may extend outside the housing 12 and allow for other components or equipment to connect with the moisture trap 10. The housing 12 may include apertures 82 (FIGS. 1 and 6) substantially aligned with the ports 18, 20 of the cooling chamber 14, with the connectors 18', 20' extending through the apertures. The connectors 18', 20' may include hose connections such as, for example, ½ inch, 7/16 inch, or ⅜ inch hose connections.

The moisture trap 10 is configured to be used in combination with a vacuum pump and equipment from which moist air is evacuated. For example, a vessel containing a wet or moist test sample can be connected to the moisture trap 10 at the port 18 or the connector 18' and a vacuum pump can be connected to the moisture trap 10 at the port 20 or the connector 20'. In some embodiments, the moisture trap 10 is configured to be used in combination with a vacuum pump having a flow rate of between about 40 liters per minute to about 200 liters per minute.

Figure 7:
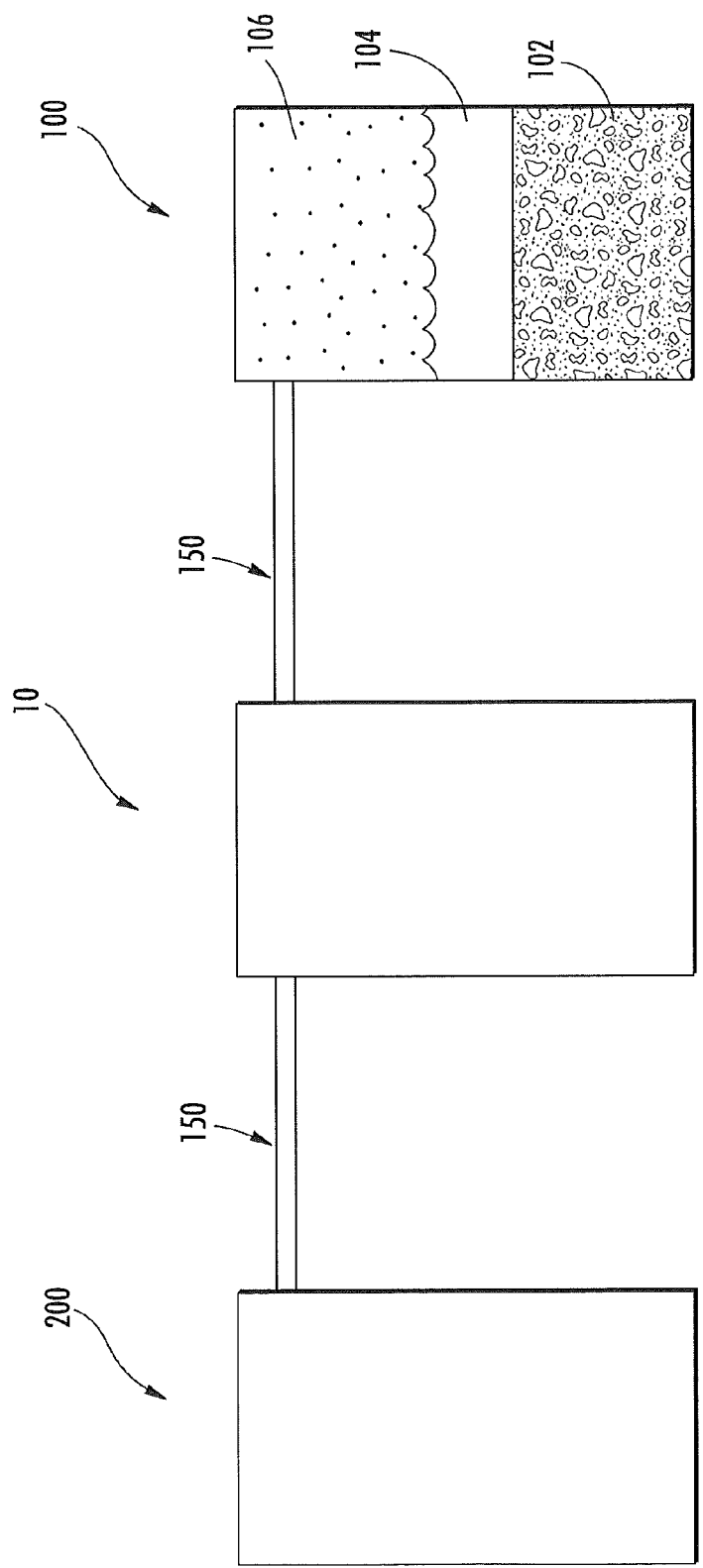
FIG. 7 is a schematic of a system using the moisture trap of FIG. 1.

This is illustrated in FIG. 7. A chamber or vessel 100 includes a test sample 102. The test sample 102 may be compacted asphalt or loose asphalt mixture, for example. The chamber 100 may include liquid 104 (e.g., water), which may submerge the test sample 102. The vessel 100 may include vapor 106 (e.g., water vapor). A fluid path 150 connects the chamber 100 and a vacuum pump 200. The portable moisture trap 10 is positioned in the fluid path 150. For example, the fluid path 150 may comprise a hose or pipe fluidly connecting the chamber 100 and the moisture trap 10 (e.g., at connector 18'), and may also comprise a hose or pipe fluidly connecting the vacuum pump 200 and the moisture trap (e.g., at connector 20').

In operation, the lid 22 is sealably attached to the top portion 14t of the cooling chamber 14 and power is supplied to the moisture trap 10. Power will activate the thermoelectric device 24. The cooling side 24c of the thermoelectric device 24 cools the cooling chamber 14. Heat generated by the heat generating side 24h of the thermoelectric device is transferred to the heat sink 26. Heat is removed from the heat sink 26 using the fan 30. As more heat is removed from the heat sink 26, more heat is transferred from the heat generating side 24h of the thermoelectric device 24, and as a result the temperature of the cooling side 24c of the thermoelectric device 24 decreases and accordingly the temperature of the cooling chamber 14 also decreases.

The cooling chamber 14 is thermally isolated from the heat generating side 24h of the thermoelectric device 24 and the heat sink 26 by the spacer block 40, and by the use of insulating materials 46, 54, and 58. This thermal isolation allows the cooling chamber 14 to become increasingly cold even as the heat generating side 24h of the thermoelectric device 24 and the heat sink 26 dissipate more and more heat.

In particular, the inner and outer bottom surfaces 34, 42 of the cooling chamber 14 and the sidewalls $14_1$, $14_2$, $14_3$, $14_4$ of the cooling chamber 14 become increasingly cold after applying power to the moisture trap 10. After a certain amount of time, the temperature of the cooling chamber 14 reaches steady state. In some embodiments, the cooling chamber 14 reaches a steady state temperature of about 32 degrees Fahrenheit at about 70 degrees Fahrenheit ambient in less than about 15 minutes.

A vacuum pump, such as the vacuum pump 200 illustrated in FIG. 7, is then operated. The vacuum pump is in fluid communication with a port of the cooling chamber 14, such as port 20. The vacuum pump is configured to evacuate moist air from equipment, such as the chamber or vessel 100 illustrated in FIG. 7. The equipment from which moist air is evacuated is in fluid communication with the opposite port of the cooling chamber 14, such as port 18.

Thus, moist air is received through the port 18 of the cooling chamber 14 in response to operation of the vacuum pump. The baffle 32 in the interior of the cooling chamber 14 serves to urge the moist air down toward the inner bottom surface 34 of the cooling chamber 14 and then up before substantially dry air exits the port 20 of the cooling chamber 14. For example, the air may take a path similar to that shown by the arrow in FIG. 2. In this regard, the baffle serves to direct the air along the relatively cold surfaces of the cooling chamber 14 to enhance moisture removal. The baffle 32 can also encourage the air to travel proximate the first sidewall of the cooling chamber 14 through which the first port 18 extends as the air travels downward from the port 18 and can also encourage the air to travel proximate the sidewall of the cooling chamber 14 through which the second port 20 extends as the air travels upward toward the port 20.

Moisture is removed from the air as it travels through the cooling chamber 14; the moisture removal is enhanced by directing the air along the relatively cold surfaces of the cooling chamber 14. Water vapor in the air condenses and collects at the inner bottom surface 34 of the cooling chamber. As described above, the lid 22 may include an optically transparent or translucent material to allow a user to observe moisture as it gathers in the cooling chamber 14. After the vacuum process has been completed, the user may open the lid 22 and remove the moisture from the cooling chamber 14, such as by absorption or suction. Additionally or alternatively, an automatic or manual valve and/or a drain may be included at the bottom of the cooling chamber to allow moisture to flow therefrom.

In some embodiments, a temperature sensor is placed in the interior of the cooling chamber 14. This can allow a user to monitor the temperature of the cooling chamber 14 and, for example, determine when the cooling chamber 14 has reached a steady state temperature. Moreover, the temperature sensor may be in communication with a controller, and the controller may also be in communication with other components (e.g., the fan 30, the power adapter 62, etc.) to regulate the temperature of the cooling chamber 14. The controller may be separate from the moisture trap 10 or may be integrated with the moisture trap 10. For example, the controller may be housed within the box 60.

The moisture trap described herein can provide several advantages over traditional moisture removing devices used in these applications. The cold temperatures and directed air flow path can remove moisture more efficiently than traditional devices. In particular, desiccant dryers may be somewhat efficient when the desiccants are initially dry; however, they may quickly lose their efficiency as the desiccants inevitably become wet from moist air flowing therethrough. Accordingly, these dryers must be continually replaced or recycled, adding cost and causing downtime. Moreover, moisture can enter the vacuum pump even when these dryers are replaced or recycled regularly.

Vacuum pumps employ lubricants such as oil to reduce friction between moving parts and to protect seals. Any moisture entering the vacuum pump serves to dilute the lubricant and reduce its effectiveness. As a result, any moisture entering the pump necessitates increased oil changes, which increase cost, produce waste, and create downtime. Moreover, the gradual breakdown of the lubricant during operation decreases the lifetime of the pump due to friction between parts and breakdown of seals.

Furthermore, the moisture trap described herein allows for a relatively unobstructed flow path through the moisture trap. This is in contrast to other dryers such as desiccant dryers, which can create considerably more resistance. The vacuum pump must work harder and requires more power input due to increased flow resistance.

The moisture trap described herein can improve the efficiency of the vacuum pump in another way: the pressure is reduced inside the cooling chamber as moisture is condensed. This creates an increased pressure gradient between the equipment to be evacuated (e.g., chamber or vessel containing moist air) and the vacuum pump, thereby increasing the efficiency of the pump.

The moisture trap can also provide an environmentally-friendly solution. Its enhanced moisture removing capabilities and relatively unobstructed air flow path can reduce the power consumption of the vacuum pump. The reduction of moisture entering the pump also increases the lifetime of the pump, therefore eliminating waste created by disposing of the pump unnecessarily early. Along the same lines, the reduction in moisture entering the vacuum pump reduces the number of required oil changes, which create oil waste that is difficult to dispose and harmful to the environment.

As described above, the configuration of the moisture trap also allows for a lightweight, portable solution. In some embodiments, the footprint of the moisture trap is less than about 100 square inches, and in other embodiments less than about 88 square inches. In some embodiments, the moisture trap weighs less than about 10 pounds, and in other embodiments weighs less than about 8 pounds.

The moisture trap is suitable to be used in laboratory applications, such as the testing of compacted and loose paving mixtures. The lightweight and portable nature of the moisture trap allow for easy manipulation and movement required in these environments. Moreover, the connectors/ports of the moisture trap can allow for easy connection of components such as vacuum pumps and vessels.

The moisture trap is also configured to be operated continuously, thereby improving the accuracy, reliability and repeatability of tests. This is in contrast to other dryers, such as desiccant dryers, that need constant replacement, increasing downtime and potentially compromising repeatability of test conditions.

The moisture trap can be used in systems designed to dry compacted asphalt samples for testing, such as the systems disclosed in U.S. Patent Application Publication No. 2005/0102851 to He et al., the disclosure of which is incorporated herein in its entirety. In particular, the moisture trap 10 can be positioned between a chamber containing an initially wet compacted asphalt sample and a vacuum pump configured to evacuate moist air from the chamber. In some embodiments, the sample in the chamber is exposed to alternating cycles of applied vacuum and ambient or heated air to keep the sample at a relatively constant temperature. For example, the chamber may include two ports, with vacuum being applied through one port and ambient air supplied through another port. At least during the vacuum cycle, the moisture trap 10 can prevent moist air evacuated from the chamber from entering the vacuum pump. In these systems, the cycling can continue until the pressure in the chamber is less than 10 TORR, which indicates that the compacted asphalt sample is dry.

The moisture trap 10 can also be used in the testing of loose asphalt mixtures. For example, the moisture trap can be used in tests for determining maximum specific gravity and density of bituminous paving mixtures. These tests are described in ASTM Test D2041 and AASHTO Test T209, the disclosures of each of which are incorporated herein in their entireties. Vacuum pumps are used in these tests to reduce the pressure in a vessel containing a test sample submerged in water (the vacuum pump is also used to remove air from the sample). The tests require the use of one or more 1000 mL filter flasks, or the equivalent, installed between the vessel and the vacuum pump to reduce the amount of water vapor entering the pump. Current practice is to use one or more desiccant dryers; however, these dryers have several drawbacks as detailed above.

Figure 8:
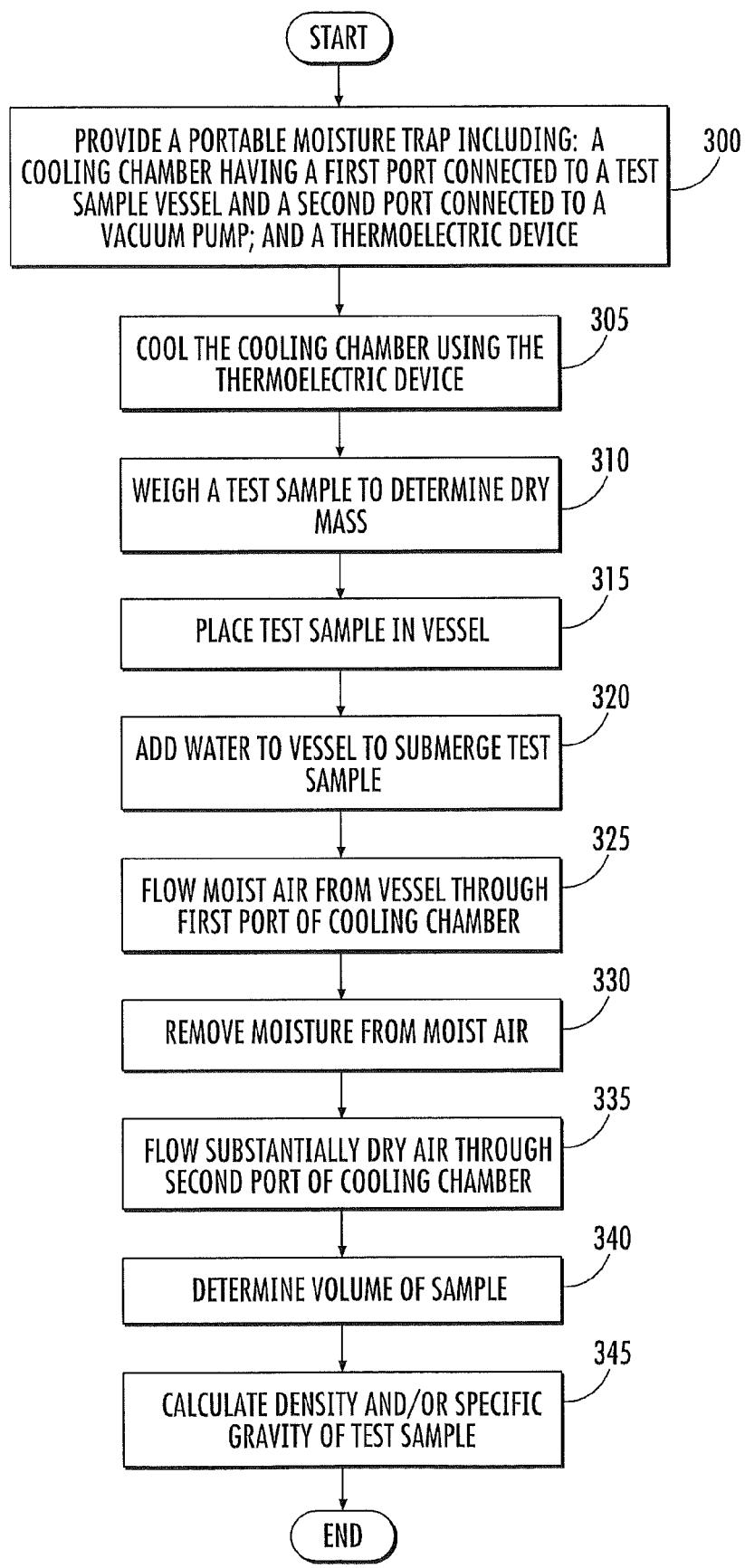
FIG. 8 is a flow chart illustrating operations using the moisture trap of FIG. 1.

FIG. 8 illustrates operations for determining the maximum specific gravity or density of a test sample using a portable moisture trap. A portable moisture trap in a fluid path connecting a vessel adapted to hold a test sample and a vacuum pump is provided (Block 300). The portable moisture trap includes a cooling chamber having a first port connected to the vessel and a second port connected to the vacuum pump. The portable moisture trap also includes a thermoelectric device. In some embodiments, the portable moisture trap can include other components described above in reference to the moisture trap 10. The cooling chamber is cooled using the thermoelectric device (Block 305). The test sample is weighed to determine a dry mass of the sample (Block 310). Subsequently, the test sample is placed in the vessel (Block 315). Water is added to the vessel to submerge the test sample (Block 320).

Moist air is evacuated from the vessel while the test sample is submerged and the pressure in the vessel is reduced using the vacuum pump. This evacuating step can be carried out by the following: flowing moist air from the vessel through the first port of the cooling chamber (Block 325); then removing moisture from the moist air in the cooling chamber (Block 330); and then flowing substantially dry air through the second port of the cooling chamber toward the vacuum pump (Block 335). In some embodiments, the cooling chamber includes a baffle extending downwardly in the cooling chamber from a location proximate a lid to a location proximate an inner bottom surface of the cooling chamber, and the step of removing moisture (Block 330) includes urging moist air down toward the inner bottom surface of the cooling chamber. In some embodiments, the baffle comprises a plate that extends across the cooling chamber and contacts opposing corners or sidewalls so that the first port is on one side of the plate and the second port is on the other side of the plate, wherein the plate has a bottom edge with alternating downward projections and valleys that resides proximate the inner bottom surface of the cooling chamber, and the step of removing moisture (Block 330) includes flowing moist air through the valleys of the baffle.

Subsequently, the volume of the sample is determined (Block 340). In some embodiments, the step of determining the volume of the sample includes: submerging the vessel with the test sample in a water bath; and determining an underwater weight of the test sample. In some other embodiments, the step of determining the volume of the sample includes: filling a known volume vessel with the sample and water; and weighing the filled vessel in air.

Finally, the density and/or specific gravity of the test sample is calculated using the determined dry mass and the determined volume of the sample (Block 345). The density is calculated by dividing the dry mass by the volume. The maximum specific gravity is the ratio of the mass of the sample to the mass of an equal volume of water.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A portable moisture trap for use with a vacuum pump, comprising: a housing, a cooling chamber positioned at least partially within the housing, the cooling chamber including a first inlet port and a second outlet port; a lid that sealably attaches to a top portion of the cooling chamber to seal the cooling chamber; a heat sink residing under the cooling chamber; a thermoelectric device having an upper cooling side and a lower heat generating side residing between the cooling chamber and the heat sink, the thermoelectric device being in thermal communication with the cooling chamber and oriented so that the cooling side faces the cooling chamber and the heat generating side faces and is in thermal communication with the heat sink; a fan residing under the heat sink, the fan oriented to blow air upwardly toward the heat sink; and a baffle extending downwardly in the cooling chamber from a location proximate the lid to a location proximate an inner bottom surface of the cooling chamber; wherein the baffle comprises a plate that extends across the cooling chamber so that the first port is on one side of the plate and the second port is on the other side of the plate, and wherein the plate has a bottom edge with alternating downward projections and valleys that resides proximate the inner bottom surface of the cooling chamber, the baffle configured to define a physical barrier to urge air received through the first port to flow down toward the inner bottom surface of the cooling chamber before exiting through the second port, to thereby remove moisture from air traveling through the cooling chamber in response to a vacuum pump in fluid communication with the second port.

2. The portable moisture trap of claim 1, wherein the cooling chamber comprises sidewalls defining corners, and wherein the baffle contacts opposing sidewalls or corners.

3. The portable moisture trap of claim 1, wherein the heat sink comprises elongated downwardly extending fins, and wherein the housing comprises one sidewall panel that has a cutaway that has a size sufficient to expose at least a major portion of a length of the downwardly extending fins of the heat sink to environmental conditions.

4. The portable moisture trap of claim 1, further comprising a power supply attached to the housing to provide power to the thermoelectric cooling device and/or the fan.

5. The portable moisture trap of claim 1, wherein the portable moisture trap has a footprint of less than about 100 square inches, and wherein the portable moisture trap weighs less than about 10 pounds.

6. The portable moisture trap of claim 1, further comprising a spacer block positioned between the cooling side of the thermoelectric device and the outer bottom surface of the cooling chamber.

7. The portable moisture trap of claim 6, wherein the thermoelectric device has a surface area that is about 2.5 square inches or less and is substantially centered on an upper surface of the heat sink, wherein the spacer block has opposing upper and lower surfaces each with a surface area that is larger than that of the thermoelectric device but less than about 4 square inches and has a thickness of between 2 inches to 5 inches and is substantially centered on the thermoelectric device, and wherein the cooling chamber has a bottom surface that has a surface area that is greater than the surface area of the spacer block upper surface and is substantially centered on the spacer block.

8. The portable moisture trap of claim 6, further comprising a first insulating material snugly surrounding downwardly extending perimeter sides of the spacer block.

9. The portable moisture trap of claim 8, wherein the first insulating material comprises a gasket with an upper portion of the gasket directly contacting a bottom surface of the cooling chamber and a lower portion of the gasket directly contacting an upper surface of the heat sink.

10. The portable moisture trap of claim 8, wherein the cooling chamber is substantially square or rectangular and includes first and second sidewalls that are substantially parallel and third and fourth sidewalls that are substantially parallel, the portable moisture trap further comprising:
    a second insulating material positioned between the first and second sidewalls of the cooling chamber and the housing; and
    a third insulating material positioned between the third and fourth sidewalls of the cooling chamber and the housing, wherein the second insulating material is different from the third insulating material.

11. The portable moisture trap of claim 10, wherein the second insulating material comprises fiberglass and the third insulating material comprises foam rubber adhesively attached to the third and fourth sidewalls of the cooling chamber.

12. The portable moisture trap of claim 10, wherein the first and second ports extend from the cooling chamber through a respective aperture in the second insulating material and through an aligned aperture in the housing.

13. The portable moisture trap of claim 1 in combination with: 1) a vessel configured to hold a moist or wet asphalt test sample, wherein the vessel is in fluid communication with the first port; and 2) a vacuum pump, wherein the vacuum pump is in fluid communication with the second port.

14. The portable moisture trap of claim 1, wherein the lid comprises an optically translucent or transparent material and is configured to pivotably or releasably sealably connect to the open top portion of the cooling chamber.

15. The portable moisture trap of claim 1, wherein the cooling chamber has an inner volume between 14 in$^3$ to 70 in$^3$.

16. The portable moisture trap of claim 1, wherein the fan is oriented in a substantially horizontal orientation.

17. The portable moisture trap of claim 1, wherein the first port extends through a sidewall of the cooling chamber, and wherein the second port extends through the same or a different sidewall of the cooling chamber.

18. A system for evaluating test samples, comprising:
    a chamber containing moist air and adapted to hold a loose aggregate or compacted asphalt sample;
    a vacuum pump in fluid communication with the chamber to evacuate moist air from the chamber;
    a fluid path connecting the chamber and the vacuum pump; and
    a portable moisture trap positioned in the fluid path to remove moisture from the evacuated air, the portable moisture trap comprising:
        a housing;
        a cooling chamber at least partially within the housing including a first port and a second port;
        a lid that sealably attaches to a top portion of the cooling chamber to seal the cooling chamber;
        a heat sink residing under the cooling chamber;
        a thermoelectric device having an upper cooling side and a lower heat generating side residing between the cooling chamber and the heat sink, the thermoelectric device being in thermal communication with the cooling chamber and oriented so that the cooling side faces the cooling chamber and the heat generating side faces and is in thermal communication with the heat sink;
        a fan residing under the heat sink, the fan oriented in a substantially horizontal orientation to blow air upwardly to remove heat from the heat sink; and
        a baffle extending downwardly in the cooling chamber from a location proximate the lid to a location proximate an inner bottom surface of the cooling chamber;
    wherein the baffle comprises a plate that extends across the cooling chamber so that the first port is on one side of the plate and the second port is on the other side of the plate, and wherein the plate has a bottom edge with alternating downward projections and valleys that resides proximate the inner bottom surface of the cooling chamber, the baffle configured to define a physical barrier to urge air received through the first port to flow down toward the inner bottom surface of the cooling chamber before exiting through the second port;
    wherein, in operation and in response to operation of the vacuum pump, moist air flows from the chamber through the first port of the cooling chamber, down, through the valleys and adjacent the inner bottom surface of the cooling chamber to remove moisture from the moist air, and substantially dry air flows through the second port of the cooling chamber to the vacuum pump.

\* \* \* \* \*